United States Patent

Paramelle et al.

Patent Number: 5,225,405
Date of Patent: Jul. 6, 1993

[54] USE OF TRIAZINE AND PYRIMIDINE COMPOUNDS FOR OBTAINING MEDICAMENTS THAT REVERSE RESISTANCE TO ANTI-CANCER AND ANTI-MALARIAL AGENTS

[75] Inventors: Bernard Paramelle; Xavier Leverve, both of La Tronche; Gilbert Regnier, Chatenay Malabry; Alain Dhainaut, Chatou; Ghanem Atassi, Saint Cloud, all of France

[73] Assignee: Adir et Compagnie, Courbevoie, France

[21] Appl. No.: 765,679

[22] Filed: Sep. 26, 1991

[30] Foreign Application Priority Data

Sep. 27, 1990 [FR] France ................. 90 11887

[51] Int. Cl.$^5$ ............ A01N 55/02; A01N 43/58; A61K 31/555; A61K 31/495
[52] U.S. Cl. ..................... 514/185; 514/248; 514/249; 514/255; 514/258; 514/259; 514/269; 514/275
[58] Field of Search ........... 544/204, 208, 209, 211, 544/212, 215, 358, 359; 514/185, 248, 249, 255, 258, 259, 269, 275

[56] References Cited

U.S. PATENT DOCUMENTS 3,647,794  3/1972  Regnier et al. ............... 544/198

Primary Examiner—Nathan M. Nutter
Attorney, Agent, or Firm—Gordon W. Hueschen

[57] ABSTRACT

The invention relates to the use, for obtaining medicaments that reverse resistance to anti-cancer and anti-malarial agents, of compounds of formula I:

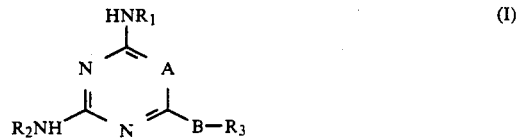

in which
A is —CH— or nitrogen,
and B, $R_1$, $R_2$ and $R_3$ are as defined in the description, and their physiologically tolerable acid addition salts.

8 Claims, No Drawings

USE OF TRIAZINE AND PYRIMIDINE COMPOUNDS FOR OBTAINING MEDICAMENTS THAT REVERSE RESISTANCE TO ANTI-CANCER AND ANTI-MALARIAL AGENTS

The present invention relates to the use of triazine and pyrimidine compounds for obtaining medicaments that reverse resistance to anti-cancer and anti-malarial agents.

A number of triazine and pyrimidine compounds having valuable pharmacological properties are known in the literature. Some of these compounds facilitate the uptake of oxygen and are used in the treatment of cerebral decline (Patents FR 2,525,597, FR 2,521,560 and FR 2,524,467). Others are used in the treatment of respiratory insufficiency (Patent FR 2,019,646) or of any type of tissue hypoxia (Patent FR 2,544,315).

The applicant has now found that some of these compounds have other very valuable pharmacological properties. In fact, they reverse, partially or completely, acquired resistance to anti-cancer agents and anti-malarial medicaments.

Resistance to anti-cancer agents is a major obstacle to the effectiveness of anti-tumour drugs. When tumour cells are exposed in vitro or in vivo to an anti-cancer agent, they become resistant, to varying degrees, to those compounds.

Many mechanisms by which a cell acquires resistance to anti-cancer agents have been described. Of the various types of resistance, "multidrug resistance" (MDR) is especially interesting. The phenomenon of resistance is due to the action of an inducible membrane protein, gP 170, whose role is to increase the efflux of the cytotoxic agent and thus reduce its intracellular concentration, hence the loss of sensitivity of those cells to the drug.

Medicaments, used in other pathologies, are known for reversing this resistance partially or completely (Int. J. Cancer Res. (1988), 79. pp. 285-296; J.N.C.I. (1989), 81, pp. 907-910; Trends Pharmacol. Sci. (1989), 9, pp. 54-58; Annu. Rev. Biochem. (1989), 58. pp. 137-171).

The modulating agent, when added at the same time as the cytotoxic agent, reduces or completely suppresses MDR-type resistance. Some medicaments which are used for the treatment of other disorders, such as amiodarone, verapamil or cyclosporin, have been used clinically to suppress this resistance, but their intrinsic pharmacological properties (hypotensive or immunosuppressive agents), which are often undesirable during the treatment of cancer, and their toxicity limit their use considerably.

The mechanism of resistance to chloroquine which has been developed by Plasmodium falciparum is similar. Verapamil restores the sensitivity of a resistant line, which demonstrates the potential value of compounds that reverse the MDR phenotype of tumour cells for use in parasitology (Science (1987), 238, pp. 1,283-1,285; Science (1987), 235, pp. 899-901).

The present invention relates especially to the use, for obtaining medicaments that reverse acquired resistance to anti-cancer and anti-malarial agents, of compounds of formula I:

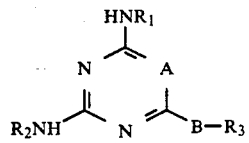

in which

A represents a group —CH— or a nitrogen atom, $R_1$ and $R_2$, which are identical or different, each represents a straight-chain or branched alkyl, each having from 3 to 5 carbon atoms and each optionally substituted by one or more hydroxy radicals, B represents a) a radical of the formula $Y_1$:

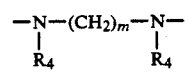

(in which $R_4$ represents a hydrogen atom or an alkyl radical having from 1 to 5 carbon atoms and m represents an integer from 2 to 6), b) a radical of the formula $y_2$:

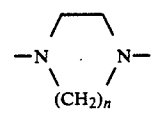

(in which n represents an integer 2 or 3), c) a radical of the formula $y_3$:

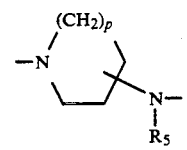

(in which p represents zero or an integer 1 or 2, and $R_5$ represents a hydrogen atom, an alkyl radical having from 1 to 5 carbon atoms, or a cycloalkyl radical having from 3 to 7 carbon atoms), or d) or a radical of the formula $y_4$:

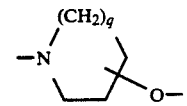

(in which q represents zero or an integer 1 or 2), $R_3$ represents:

a) a diphenylmethyl radical optionally substituted on the benzene rings by one or more halogen atoms, b) a radical of the formula $z_1$:

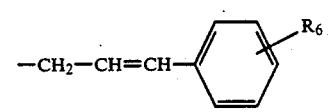

(in which $R_6$ represents a hydrogen atom or a halogen atom), c) a radical of the formula $z_2$:

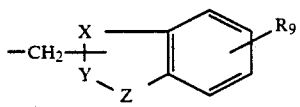

(in which —X—Y— represents a radical of the formula $$-CH=CH-(CR_7R_8)_r-,$$

in which r represents 0 or 1 and $R_7$ and $R_8$, which are identical or different, each represents a hydrogen atom or a methyl radical, Z represents an oxygen or sulphur atom and $R_9$ represents a hydrogen atom or a halogen atom), or d) (when B is a radical of the formula $Y_3$ or a radical of the formula $Y_4$) a radical of the formula $z_3$:

$$-SO_2R_{10} \quad (z_3)$$

(in which $R_{10}$ represents an alkyl radical having from 1 to 3 carbon atoms, or a phenyl radical), and their addition salts obtained with a therapeutically compatible mineral or organic acid.

There may be mentioned as acids used for the formation of addition salts hydrochloric acid, sulphuric acid, hydrobromic acid, phosphoric acid, acetic acid, propionic acid, maleic acid, benzoic acid and methanesulfonic acid.

The medicaments obtained using, in accordance with the invention, the compounds of formula I or their pharmaceutically acceptable salts will be presented in pharmaceutical forms suitable for administration orally, parenterally, percutaneously or transcutaneously, such as, for example, tablets, soft gelatin capsules, lozenges and injectable or drinkable solutions.

The dosage can vary widely according to the age and weight of the patient, the mode of administration and the nature of the disorder and the associated treatments, and ranges from 0.10 to 7 g per dose.

The pharmacological activities of the compounds of formula I described in Patents FR 2,525,597, FR 2,521,560 FR 2,524,467, FR 2,019,646 and FR 2,544,315 gave no indication at all of the very valuable properties discovered by the applicant. The prior-known activities do not, however, constitute a limiting factor for the use of the compounds of formula I during anti-cancer or anti-malarial treatment. Moreover, the toxicity of the compounds of formula I is very low, which enables them to be administered at very high doses.

The following products may be mentioned as examples of compounds of formula I:

Compound 1
1-(4,6-bis-allylamino-1,3,5-triazin-2-yl)-3-(bis-para-fluorobenzhydrylamino)piperidine difumarate Compound 2
1-(4,6-bis-allylamino-1,3,5-triazin-2-yl)-4-(benzofuran-2-ylmethylamino)piperidine difumarate Compound 3
1-(4,6-bis-allylamino-1,3,5-triazin-2-yl)-4-(5-fluorobenzofuran-2-ylmethyl)piperazine Compound 4
1-(4,6-bis-allylamino-1,3,5-triazin-2-yl)-4-(bis-para-fluorobenzhydryloxy)piperidine hydrochloride Compound 5
N,N'-diethyl-N-(4,6-bis-allylamino-1,3,5-triazin-2-yl)-N'-(benzothien-2-ylmethyl)ethylenediamine fumarate Compound 6
1-(4,6-bis-allylamino-1,3,5-triazin-2-yl)-4-(N-bisparafluorobenzhydryl-N-ethylamino)piperidine difumarate Compound 7
1-(4,6-bis-allylamino-1,3,5-triazin-2-yl)-4-(bis-para-fluorobenzhydrylamino)piperidine difumarate Compound 8
1-(4,6-bis-allylamino-1,3,5-triazin-2-yl)-4-(benzothien-2-ylmethylamino)piperidine difumarate Compound 9
1-(4,6-bis-allylamino-1,3,5-triazin-2-yl)-4-(para-fluorobenzhydrylamino)piperidine dihydrochloride Compound 10
1-(4,6-bis-allylamino-1,3,5-triazin-2-yl)-4-benzhydrylaminopiperidine difumarate Compound 11
1-(4,6-bis-allylamino-1,3,5-triazin-2-yl)-4-(para-fluorobenzhydryl)piperazine methanesulfonate The following Examples illustrate the invention.

EXAMPLE 1

Evaluation of the increase of the cytotoxicity of adriamycin on the line P 388/ADR-1 in vitro In this study, the cytotoxicity of adriamycin was measured in the absence and in the presence of the reversing compound. Murine leukaemia P 388/ADR-1 was used for this test, and its resistance was induced by adriamycin. Its resistance factor is 40 in comparison with the sensitive line (average resistance).

The cells are cultured in a complete culture medium (RPMI 1640) containing 10% foetal calf serum, 2 nM of glutamine, 50 IU/ml of penicillin, 50 µg/ml of streptomycin, 10 mM of Hepes and 20 nM of beta-mercaptoethanol.

The cells are distributed on microplates and exposed to adriamycin at 9 different concentrations.

The products tested for their ability to reverse MDR are added at the same time as the cytotoxic agent. The cells are then incubated for 48 hours.

The number of viable cells is then quantified by means of a colorimetric assay, the Microculture Tetrazolium Assay (Cancer Res. (1987), 47, pp. 936–942).

The results are expressed as IC50, which is the concentration of cytotoxic agent that inhibits the proliferation of the control cells by 50%. The results are expressed as the Reversion Factor (RF).

$$RF = \frac{IC_{50} \text{ of the cytotoxic agent on its own}}{IC_{50} \text{ of the cytotoxic agent in the presence of the reversing compound}}$$

Table I shows the values of the reversion factors obtained with the various compounds of formula I and the reference products, and demonstrates the very interesting activity of the compounds of formula I.

With regard to reserpine (one of the reference products), that compound exhibits very good activity in vitro but cannot be used in vivo on account of its high toxicity.

TABLE I

| COMPOUNDS | 2.5 µM | 5 µM | 10 µM | 20 µM |
|---|---|---|---|---|
| REFERENCE PRODUCTS | | | | |
| PHENOTHIAZINE | — | 0.5 | 0.5 | 0.4 |

TABLE I-continued

| COMPOUNDS | 2.5 μM | 5 μM | 10 μM | 20 μM |
|---|---|---|---|---|
| CHLOROPROMAZINE | — | 2.6 | 3.8 | TOX |
| YOHIMBINE | — | 0.4 | 0.9 | 2.1 |
| NIFEDIPINE | — | 1.0 | 2.2 | 2.1 |
| PROGESTERONE | — | 0.6 | 0.7 | 2.1 |
| QUININE | — | 0.8 | 2.0 | 2.1 |
| DILTIAZEM | — | 3.1 | 6.1 | 6.5 |
| FLUNARIZINE | — | 1.5 | 2.9 | 6.9 |
| DIPYRIDAMOLE | — | 2.2 | 4.2 | 8.5 |
| QUINIDINE | — | 0.8 | 2.5 | 3.5 |
| QUINACRINE | — | 3.4 | TOX* | TOX |
| TRIFLUOPERAZINE | — | 2.9 | TOX | TOX |
| VERAPAMIL | — | 7.5 | 1.7 | 14.5 |
| AMIODARONE | — | 8.1 | 1.6 | TOX |
| PIMOZIDE | 7.9 | 19.3 | TOX | TOX |
| RESERPINE | 41 | 42 | 35 | TOX |
| CYCLOSPORIN | — | 21 | 23 | TOX |
| COMPOUNDS OF FORMULA I | | | | |
| COMPOUND 6 | 24.4 | 27.0 | 20.7 | 41.1 |
| COMPOUND 7 | 10.3 | 17.3 | 40.9 | — |
| COMPOUND 9 | 6.9 | 16.3 | 51.2 | — |
| COMPOUND 10 | 12.4 | 27.3 | 26.7 | — |
| COMPOUND 11 | 11.5 | 24.3 | 34.5 | 144 |

*The compounds are considered to be toxic when the cell toxicity is ≧50%.

EXAMPLE 2

Evaluation of the increase of the cytotoxicity of actinomycin D on the Chinese hamster lung line DC-3F/AD The protocol used for this study is identical to that used for the test described in Example 1, but the culture medium did not contain beta-mercaptoethanol and the cells were incubated for 4 days instead of for 48 hours. The cytotoxic agent used was actinomycin D.

The line DC-3F/AD is an extremely resistant line. Its resistance factor is greater than 10,000.

The results of this study are shown in Table II.

The results given in Table II show that the compounds of formula I reduce significantly or suppress resistance to the cytotoxic agent.

TABLE II

| COMPOUNDS | 2.5 μM | 5 μM | 10 μM | 20 μM |
|---|---|---|---|---|
| REFERENCE PRODUCTS | | | | |
| PHENOTHIAZINE | — | <12 | <12 | <12 |
| CHLOROPROMAZINE | — | <13 | <13 | <13 |
| YOHIMBINE | — | <12 | <12 | <12 |
| NIFEDIPINE | — | <11 | TOX | TOX |
| PROGESTERONE | — | <10 | <10 | 13 |
| QUININE | — | <10 | <10 | <11 |
| DILTIAZEM | — | <11 | <10 | <11 |
| FLUNARIZINE | — | <13 | 16 | TOX |
| DIPYRIDAMOLE | — | <12 | <11 | <12 |
| QUINIDINE | — | <12 | <12 | <12 |
| QUINACRINE | — | <13 | <12 | TOX |
| TRIFLUOPERAZINE | — | <12 | 38 | TOX |
| VERAPAMIL | — | <13 | 31 | 117 |
| AMIODARONE | — | 365 | 276 | TOX |
| PIMOZIDE | <10 | 28 | 1649 | TOX |
| RESERPINE | 258 | 1085 | <11 | 2024 |
| CYCLOSPORIN | <11 | <11 | 23 | 10 |
| COMPOUNDS OF FORMULA I | | | | |
| COMPOUND 1 | <18 | 118 | 263 | 2283 |
| COMPOUND 2 | — | 450 | 451 | 2148 |
| COMPOUND 3 | — | 340 | 831 | 2189 |
| COMPOUND 4 | — | 290 | 970 | 3302 |
| COMPOUND 5 | <15 | <15 | 1013 | 4059 |
| COMPOUND 6 | — | — | 1093 | 3744 |
| COMPOUND 7 | — | 388 | 1212 | 3056 |
| COMPOUND 8 | — | 310 | 1281 | 7327 |
| COMPOUND 9 | — | 732 | 1796 | 13657 |
| COMPOUND 10 | — | 905 | 1828 | 3313 |

EXAMPLE 3

Flow cytometry

Some anti-cancer compounds, such as adriamycin (ADR), have the property of being fluorescent after excitation by a light source of known wavelength.

By measuring this fluorescence, it is possible to measure in a relative manner the intracellular concentration of ADR. Flow cytometry (FCM) is an excellent tool for carrying out this type of measurement and thus determining rapidly whether certain active compounds act by increasing the intracellular concentration of adriamycin.

The cells (500×10³ per ml) were exposed simultaneously to adriamycin in a fixed concentration (50 μM) and to the test compounds in concentrations of 2.5, 10 and 20 μM. After incubation for 5 hours, the uptake of adriamycin into the cells was evaluated by FCM.

The analyses were carried out on an ATC 3000 flow cytometer (Bruker—France) equipped with a 2025 argon laser (Spectra-Physics-France ®) optimised at 488 nm for a power of 600 mW.

The analysis of each sample was carried out on a total of 10,000 cells at a speed of 1000 cells/second.

The results were collected in the form of linear histograms of the fluorescence of intracellular ADR.

Expression of the results: For each histogram, the mean fluorescence band (MEAN) was determined by the computer system of the apparatus.

For all experiments::
A negative control (cells without ADR) fixed the autofluorescence threshold.
A positive control (cells with ADR) determined the MEAN value=MN1.
The "test" tubes (cells with ADR and with product) determined the MEAN values=MN2 for each of the products at each of the concentrations.

The results are expressed as the variation in the mean fluorescence obtained for each of the "test" tubes (MN2) in comparison with the mean fluorescence obtained with the positive control (MN1): VAR-MEAN=MN2−MN1. The parameter expressed is thus the increase in the fluorescence of adriamycin in the presence of the test compounds.

Table III shows the increase in the fluorescence of ADR obtained with the various compounds on line DC-3F/AD, and Table IV shows that obtained on line P 388/ADR-1.

TABLE III

| COMPOUNDS | 2.5 μM | 5 μM | 10 μM | 20 μM |
|---|---|---|---|---|
| REFERENCE PRODUCTS | | | | |
| VERAPAMIL | 2.00 | 2.60 | 7.55 | 11.45 |
| AMIODARONE | 8.80 | 16.65 | 21.55 | 26.35 |
| PIMOZIDE | 5.85 | 8.85 | 15.65 | 21.60 |
| RESERPINE | 26.18 | 29.43 | 31.73 | 29.95 |
| CYCLOSPORIN | 1.90 | 3.20 | 8.05 | 15.10 |
| COMPOUNDS OF FORMULA I | | | | |
| COMPOUND 2 | 1.60 | 2.70 | 23.00 | 20.30 |
| COMPOUND 4 | 4.60 | 11.40 | 16.10 | 20.60 |
| COMPOUND 6 | 31.30 | 42.70 | 44.70 | 52.10 |

TABLE IV

| COMPOUNDS | 2.5 μM | 5 μM | 10 μM | 20 μM |
|---|---|---|---|---|
| REFERENCE PRODUCTS | | | | |
| PHENOTHIAZINE | 0.00 | 0.00 | 0.00 | 0.00 |
| CHLOROPROMAZINE | 3.30 | 5.15 | 4.60 | 6.20 |
| YOHIMBINE | 2.30 | 0.05 | 4.70 | 3.45 |
| NIFEDIPINE | 0.00 | 0.80 | 5.95 | 3.40 |
| PROGESTERONE | 1.85 | 1.00 | 6.85 | 11.80 |
| QUININE | 4.85 | 5.40 | 12.00 | 18.90 |
| DILTIAZEM | 3.10 | 6.65 | 13.45 | 23.15 |
| FLUNARIZINE | 7.35 | 10.10 | 19.90 | 41.00 |
| DIPYRIDAMOLE | 2.35 | 7.55 | 21.75 | 40.00 |
| QUINIDINE | 6.65 | 12.80 | 22.00 | 29.90 |
| QUINACRINE | 11.83 | 15.73 | 27.73 | 52.77 |
| TRIFLUOPERAZINE | 11.45 | 14.75 | 34.55 | 51.05 |
| VERAPAMIL | 9.89 | 21.90 | 39.62 | 56.50 |
| AMIODARONE | 33.40 | 65.25 | 76.33 | 95.85 |
| PIMOZIDE | 25.60 | 49.42 | 73.13 | 73.64 |
| RESERPINE | 73.46 | 80.48 | 91.90 | 85.39 |
| CYCLOSPORIN | 79.43 | 97.63 | 96.68 | 90.27 |
| COMPOUNDS OF FORMULA I | | | | |
| COMPOUND 2 | 28.45 | 45.30 | 65.20 | 70.20 |
| COMPOUND 4 | 55.20 | 77.10 | 84.06 | 94.70 |
| COMPOUND 6 | 73.75 | 88.65 | 92.00 | 95.50 |
| COMPOUND 7 | 43.55 | 66.20 | 82.48 | 91.70 |
| COMPOUND 8 | 23.75 | 43.10 | 67.05 | 71.40 |
| COMPOUND 9 | 50.10 | 69.65 | 81.65 | 83.90 |
| COMPOUND 10 | 47.75 | 68.90 | 83.03 | 85.00 |
| COMPOUND 11 | 30.15 | 70.60 | 82.86 | — |

Tables III and IV show that the compounds of formula I increase the intracellular concentration of adriamycin and are as active as cyclosporin and amidarone.

EXAMPLE 4

Pharmaceutical composition

| Soft gelatin capsules containing 200 mg of active ingredient | |
|---|---|
| Compound 11 | 200 mg |
| Cornstarch | 50 mg |
| Lactose | 100 mg |
| Talc | 30 mg |

We claim:

1. A method for reversing acquired resistance to anti-cancer and anti-malarial agents, in a living animal, which consists in administering, to the said living animal, an amount of a compound selected from those of formula I, which is effective for reversing the said acquired resistance, the compounds of formula I being identified as follows:

$$\text{(I)}$$

in which

A represents —CH— nitrogen, $R_1$ and $R_2$, which are identical or different, each represents a straight-chain or branched ($C_3$–$C_5$)-alkyl, -alkenyl, or -alkadienyl, which is optionally substituted by one or more hydroxy, B represents:

a)

$$-\underset{R_4}{N}-(CH_2)_m-\underset{R_4}{N}- \quad (y_1)$$

in which $R_4$ represents hydrogen or ($C_1$–$C_5$) alkyl and m is an integer of 2 to 6, inclusive, b)

$$(y_2)$$

in which n is 2 or 3, $$(y_3)$$

in which p is zero, 1, or 2, and $R_5$ represents hydrogen, ($C_1$–$C_5$) alkyl, or ($C_3$–$C_7$) cycloalkyl, or d)

$$(y_4)$$

in which q is zero, 1, or 2, and $R_3$ represents:

a) diphenylmethyl optionally substituted on the benzene rings by one or more halogen, b)

$$-CH_2-CH=CH-\underset{}{\phantom{x}}-R_6 \quad (z_1)$$

in which $R_6$ represents hydrogen or halogen, c)

$$(z_2)$$

in which X—Y— represents —CH=CH—(CR$_7$R$_8$)r—, in which r represents 0 or 1 and $R_7$ and $R_8$, which are identical or different, each represent hydrogen or methyl, Z represents oxygen or sulphur, and $R_9$ represents hydrogen or halogen, or d) when B is $Y_3$ or $Y_4$, $R_3$ further can represent:

$$-SO_2R_{10} \quad (z_3)$$

in which $R_{10}$ represents ($C_1$–$C_3$) alkyl or phenyl, and a physiologically-tolerable acid addition salt thereof.

2. A method of claim 1 wherein the compound of formula I is administered in the form of a pharmaceutical composition containing 0.1 to 7 g of the said compound of formula I, in admixture or association with a pharmaceutically-acceptable excipient or carrier.

3. A method according to claim 1, wherein the compound is administered in association with another cytotoxic or anti-malarial agent.

4. A method of claim 1 wherein the compound is selected from 1-(4,6-bis-allylamino-1,3,5-triazin-2-yl)-4-(parafluorobenzhydryl)piperazine and a pharmaceutically-acceptable acid addition salt thereof.

5. A method according to claim 1 wherein the compound is administered at a dose of 0.1 to 7 g.

6. A method according to claim 4 wherein the compound is administered at a dose of 0.1 to 7 g.

7. A method of claim 4 wherein the compound is administered in the form of a pharmaceutical composition containing 0.1 to 7 g of the said compound in admixture or association with a pharmaceutically-acceptable excipient or carrier.

8. A method according to claim 4, wherein the compound is administered in association with another cytotoxic or anti-malarial agent.

* * * * *

UNITED STATES PATENT AND TRADEMARK OFFICE
CERTIFICATE OF CORRECTION

PATENT NO. : 5,225,405

DATED : July 6, 1993

INVENTOR(S) : Bernard Paramelle, Xavier Leverve, Gilbert Regnier, Alain Dhainaut, Ghanem Atassi, Alain Pierre It is certified that error appears in the above-indentified patent and that said Letters Patent is hereby corrected as shown below:

Title page, [75] Inventors; line 4; change the comma "," after "Cloud" to a semicolon ";" and insert -- Alain Pierre, Marley LeRoi, --.

Column 3, approximately line 12; "$R_8)_r$ —," should read -- $R_8)_r$-, --.

Signed and Sealed this

Tenth Day of May, 1994

BRUCE LEHMAN

Attest:

Attesting Officer

Commissioner of Patents and Trademarks